(12) United States Patent
Beattie

(10) Patent No.: US 9,358,290 B2
(45) Date of Patent: Jun. 7, 2016

(54) PHARMACEUTICAL FORMULATIONS

(71) Applicant: MOREX DEVELOPMENT PARTNERS LLP, London (GB)

(72) Inventor: Chris Beattie, Farnham (GB)

(73) Assignee: Morex Development Partners LLP, London (GB)

( * ) Notice: Subject to any disclaimer, the term of this patent is extended or adjusted under 35 U.S.C. 154(b) by 0 days.

(21) Appl. No.: 14/646,527

(22) PCT Filed: Nov. 22, 2013

(86) PCT No.: PCT/EP2013/074490
§ 371 (c)(1),
(2) Date: May 21, 2015

(87) PCT Pub. No.: WO2014/079977
PCT Pub. Date: May 30, 2014

(65) Prior Publication Data
US 2015/0297717 A1   Oct. 22, 2015

(30) Foreign Application Priority Data
Nov. 23, 2012 (GB) .................................. 1221125.6

(51) Int. Cl.
| | |
|---|---|
| *A61K 31/555* | (2006.01) |
| *A61K 49/04* | (2006.01) |
| *A61K 51/00* | (2006.01) |
| *C07D 487/22* | (2006.01) |
| *A61K 41/00* | (2006.01) |
| *A61K 51/04* | (2006.01) |
| *A61K 49/06* | (2006.01) |

(52) U.S. Cl.
CPC ......... *A61K 41/0038* (2013.01); *A61K 41/0057* (2013.01); *A61K 41/0095* (2013.01); *A61K 51/0485* (2013.01); *A61K 31/555* (2013.01); *A61K 49/06* (2013.01); *C07D 487/22* (2013.01)

(58) Field of Classification Search
CPC ..... A61K 31/555; A61K 51/00; A61K 49/04; A61K 49/06; A61M 36/14; A61P 35/04
USPC ............................. 424/1.11, 1.61; 540/1, 145
See application file for complete search history.

(56) References Cited

U.S. PATENT DOCUMENTS

2008/0131376 A1* 6/2008 Miura ................ A61K 41/0019
424/9.3
2008/0233047 A1* 9/2008 Miura ................ A61K 41/0095
424/1.65

FOREIGN PATENT DOCUMENTS

| EP | 2194027 A1 | 6/2010 | |
|---|---|---|---|
| WO | WO 90/00393 | 1/1990 | |
| WO | WO 03/039597 A1 | 5/2003 | |
| WO | WO 2008133664 A2 * | 11/2008 | ......... A61K 41/0019 |
| WO | WO 2010/047611 | 4/2010 | |
| WO | WO 2014/009496 | 1/2014 | |

OTHER PUBLICATIONS

International Search Report and Written Opinion for International Patent Application No. PCT/EP2013/074490 mailed Mar. 6, 2014, from the European Patent Office.
Patents Act 1977: Search Report under Section 17(5) for corresponding GB Patent Application No. GB 1221125.6 mailed Mar. 13, 2013, from the GB Intellectual Property Office.
Muniappan et al., "Poly[[[μ-5,0,15,20-tetrakis-(4-methoxycarbonylphenyl)-porphyrinato(2-)]zinc(II)]N,N'-dimethylacetamide disolvate]," Acta Cryst. C62, m495-m497 (2006).

* cited by examiner

*Primary Examiner* — Kamal Saeed
*Assistant Examiner* — Janet L Coppins
(74) *Attorney, Agent, or Firm* — Finnegan, Henderson, Farabow, Garrett & Dunner LLP

(57) ABSTRACT

The invention provides a pharmaceutical composition comprising (a) a compound of the formula (1), wherein $R_1$, $R_2$, $R_3$ and $R_4$ are substituents, at least one of which contains a carborane cluster; and M is selected from two hydrogen ions and one or two metal ions, wherein any metal ions present are charge-balanced by one or more counter ions; and (b) a vehicle comprising: (i) dimethylacetamide as solvent; and (ii) a co-solvent comprising one or more of tetraglycol; propylene glycol; polyethylene glycol; and a non-ionic surfactant. The pharmaceutical compositions are useful as radiation sensitizers in radiation treatment of cancers.

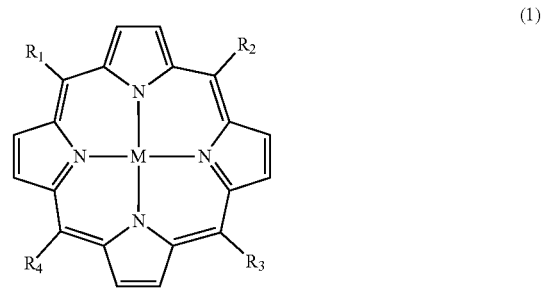

(1)

20 Claims, No Drawings

PHARMACEUTICAL FORMULATIONS

This is a national stage application under 35 U.S.C. §371 of International Application No. PCT/EP2012/074490, filed Nov. 22, 2013, which designated the U.S. and which claims the benefit under 35 U.S.C. §119 of GB 1221125.6, filed Nov. 23, 2012, all of which are incorporated herein by reference.

FIELD

The present invention relates to pharmaceutical compositions comprising carborane-containing metallo-porphyrins that are useful as radiosensitisers in radiation therapy for cancer.

BACKGROUND

Many approaches can be taken in the treatment of cancer. One approach is the use of radiosensitisers along with radiation therapy. This two-pronged approach increases the likelihood of success of the cancer therapy. Radiosensitisers are compounds which when administered to the patient make the tumour more sensitive to radiotherapy or act as an oxygen mimic such that they increase the free radicals available following the ionising radiation. The latter type of compound results in the repair mechanisms within the cell being overwhelmed and cell death occurring.

Radiosensitisers involve time-consuming administration by a specialist, which is expensive for the medical institution involved in the treatment. The radiosensitisers are generally given intravenously or by injection in large fluid volumes that take a significant amount of time to administer and a single dose may involve administration over more than one day. The invasive nature of the administration can lead to multiple puncture sites that are at risk of infection.

Most importantly, administration of the radiosensitiser is distressing to the patient. However, in order to maintain therapeutically effective levels within the tumours radiosensitisers that enhance sensitivity to radiation may be administered on a daily basis. Daily irradiation then takes place afterwards. Some cytotoxics that are used as radiosensitisers may be administered less frequently, generally once every 3-4 days or at least once per week (e.g. Cisplatin).

Compared to the administration of the radiosensitiser, irradiation is a relatively simple step. Irradiation often takes place for five days and then the patient has two days off before the cycle is repeated until the course of treatment devised by the patient's clinician is finished. The length of the course of treatment will depend, among other things, upon the patient, the type of cancer and the stage of cancer.

Examples of radiosensitisers for use in treating cancer include boron-containing compounds, and more particularly the carborane-containing nitroporphyrin compounds disclosed in WO 2008/133664.

THE INVENTION

The present invention provides improved formulations of carborane-containing porphyrin compounds and in particular formulations which provide enhanced solubilisation of the porphyrin compound in aqueous media.

Accordingly, in a first aspect, the present invention provides a pharmaceutical composition comprising:
(a) a compound of the formula (1):

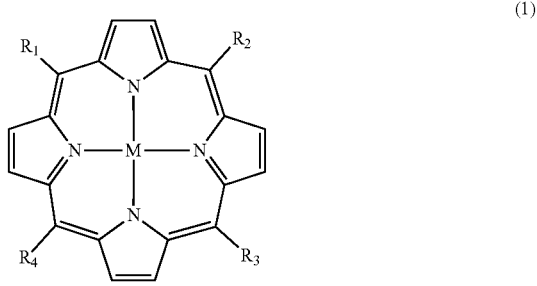

wherein:
$R^1$, $R^2$, $R^3$, and $R^4$ are selected from an electron withdrawing group, $-NO_2$, $-NH_2$, halogen, or a substituent represented by the following formula

wherein Y can be on the ortho, meta or para position on the phenyl rings, and is selected from hydrogen, hydrocarbyl, non-aromatic carbocyclic, non-aromatic heterocyclic, aryl, alkylaryl, arylalkyl; or a hydrocarbyl, non-aromatic carbocyclic, non-aromatic heterocyclic, aryl, alkylaryl, or arylalkyl group substituted with 1 to 4 hydrophilic groups selected from hydroxy, alkoxy, $-C(O)OR^5$, $-SOR^6$, $-SO_2R^6$, nitro, amido, ureido, carbamato, $-SR^7$, $-NR^8R^9$, or poly-alkyleneoxide; or a substituent represented by formula (3)

provided that at least one of $R^1$, $R^2$, $R^3$, and $R^4$ is the substituent represented by formula (2) wherein Y represents formula (3);

wherein:
X is selected from oxygen and sulphur;
$R^5$, $R^6$, $R^7$, $R^8$, $R^9$, $R^{10}$, and $R^{11}$ are selected from hydrogen and $C_1$ to $C_4$ hydrocarbyl;
Z is a carborane cluster comprising at least two carbon atoms and at least three boron atoms, or at least one carbon atom and at least five boron atoms, within a cage structure;
r is 0 or an integer from 1 to 20;
a represents an integer from 1 to 4; and
provided also that at least one of $R^1$, $R^2$, $R^3$, and $R^4$ is an electron withdrawing group, $-NO_2$, $-NH_2$, or halogen; and
M is selected from two hydrogen ions, a single monovalent metal ion, two monovalent metal ions, a divalent metal ion, a trivalent metal ion, a tetravalent metal ion, a pentavalent metal ion, and a hexavalent metal ion, wherein the porphyrin-metal complex derived from a single monovalent metal ion is charge-balanced by a counter cation, and the porphyrin-metal complex derived from a trivalent, tetravalent, pentavalent, or hexavalent metal ion is charge-balanced by an appropriate number of counter anions, dianions, or trianions; and (b) a vehicle comprising:
  (i) dimethylacetamide as solvent; and
  (ii) a co-solvent comprising one or more pharmaceutically acceptable glycol or surfactant components.

The co-solvent in embodiments of the invention comprises (i) a glycol, (ii) a surfactant, or (iii) a glycol and a surfactant.

According to the invention, the pharmaceutical compositions contain a compound of the general formula (1). In embodiments of the invention, at least one of $R^1$, $R^2$, $R^3$ and $R^4$ is a halogen. The halogen can be selected from chlorine, fluorine, bromine, and iodine, and is preferably bromine.

At least one of $R^1$, $R^2$, $R^3$ and $R^4$ can be selected from —$NO_2$ and Formula (2). In certain embodiments of the invention, at least two of $R^1$, $R^2$, $R^3$ and $R^4$ are selected from —$NO_2$ and formula (2). For example, two of $R^1$, $R^2$, $R^3$ and $R^4$ can be —$NO_2$ and two of $R^1$, $R^2$, $R^3$ and $R^4$ can be Formula (2).

In particular embodiments, $R^1$ and $R^3$ are $NO_2$ and $R^2$ and $R^4$ are Formula (2).

In embodiments of the invention $R^1$ and $R^3$ are in trans positions.

Y is suitably a hydrocarbyl group. The hydrocarbyl group can be a straight chain or branched hydrocarbyl group containing 1 to 20 carbon atoms including, optionally, up to three double bond or triple bonds. Preferably the hydrocarbyl group is an acyclic hydrocarbyl group selected from methyl, ethyl, n-propyl, iso-propyl, n-butyl, iso-butyl, sec-butyl, tert-butyl, propenyl, 2-butenyl, 3-butenyl, 3-butynyl, 2-methyl-2-butenyl, n-pentyl, dodecyl, hexadecyl, octadecyl, and eicosyl.

The hydrocarbyl group may be unsubstituted or substituted with as many hydrophilic groups that the hydrocarbyl group can tolerate, preferably between 1 and 4. Preferably the hydrophilic group is selected from hydroxy, alkoxy, —C(O)$OR^5$, —$SOR^6$, —$SO_2R^6$, nitro, amido, ureido, carbamato, —SR', —$NR^8R^9$, and poly-alkyleneoxide. Preferably, $R^5$, $R^6$, $R^7$, $R^8$, and $R^9$ are independently selected from hydrogen and hydrocarbyl groups as defined above, except that the hydrocarbyl groups for $R^5$, $R^6$, $R^7$, and $R^8$ contain 1 to 4 carbon atoms.

The carbon atoms of the hydrocarbyl group may also be substituted with 1 to 4 heteroatoms. Herein, heteroatoms are O, S, N, or $NR^{10}$. $R^{10}$ is selected from hydrogen and hydrocarbyl groups as defined above. The heteroatoms are generally not adjacent, and are preferably separated from each other by at least one carbon atom. Preferably, there is no more than one heteroatom for each two carbon atoms.

Y can be a non-aromatic carbocyclic or heterocyclic ring. Preferably, the non-aromatic carbocyclic or heterocyclic ring is a 4-, 5-, 6-, 7-, or 8-membered carbocyclic or heterocyclic ring. The ring may be saturated, or may contain as many unsaturated (i.e., double or triple) bonds as a carbocyclic ring can tolerate.

The saturated carbocyclic ring may be selected from cyclobutane, cyclopentane, cyclohexane, and cyclopentane rings. Preferably, the unsaturated carbocyclic ring is selected from cyclobutene, cyclopentene, cyclohexene, and 1,3-cycloheptadiene rings.

Preferably, Y is a heterocyclic ring. Preferably, the heterocyclic ring comprises as many heteroatoms, i.e. O, S, N, or $NR^{10}$, as the heteroatom can tolerate, e.g. 1 to 4. Preferably the saturated and unsaturated non-aromatic heterocyclic ring is selected from pyrrolidinyl, piperidine, piperazine, tetrahydrofuran, furan, thiophene, 1,3-oxazolidine, imidazole, and pyrrole rings. Preferably, the heterocyclic ring may be optionally substituted with hydrocarbyl as defined above, or with 1 to 4 hydrophilic groups, also as defined above.

Y can be a non-aromatic carbocyclic or heterocyclic ring. Preferably, the non-aromatic carbocyclic or heterocyclic ring may be a bicyclic ring. Preferably the carbocyclic ring is selected from bicycico[2.2.2.]octane, bicyclo[3.1.1.]heptane, bicyclo[3.3.0.]octane, and bicyclo[4.3.0]non-3-ene. Preferably the non-aromatic heterocyclic ring is selected from 1,4 azabicyclo[2.2.2.]octane and 2-azabicyclo[3.1.1.]heptane.

Y can be an aryl group. Preferably, the aryl group can be either aromatic carbocyclic or heterocyclic group. An aromatic carbocyclic ring is preferably phenyl. The aryl ring may be optionally substituted with hydrocarbyl as defined above to produce alkylaryl or arylalkyl groups. Preferably, the aryl, alkylaryl, and arylalkyl group may be substituted with 1 to 4 hydrophilic groups, as defined above.

Y may be an aromatic heterocyclic ring. Preferably, the aromatic heterocyclic ring comprises 1 to 4 heteroatoms, i.e. O, S, N, or $NR^{10}$. Preferably the ring is typically 5-, 6-, or 7-membered. Preferably, the aromatic heterocyclic ring is selected from thiophene, pyridine, oxazole, thiazole, oxazine, and pyrazine rings. The aromatic heterocyclic ring may be substituted with 1 to 4 hydrophilic groups, as defined above.

Preferably any of the above rings may also be fused to 1 to 3 additional 5-, 6-, or 7-membered aryl rings. Preferably the fused rings are selected from napthalene, anthracene, phenanthrene, triphenylene, chrysene, indoline, quinoline, and tetraazanaphthalene (pteridine) rings.

Y can be an alkoxy group. Preferably, the alkoxy group contains a hydrocarbyl portion as defined above. Preferably the alkoxy groups are selected from methoxy, ethoxy, propoxy, n-butoxy, t-butoxy, and dodecyloxy.

Y can be a polyalkylene oxide. Preferably, the polyalkylene oxide is defined according to the formula —$(CH_2)_d$—O—$[(CH_2)_e$—O—$]_x$—$[(CH_2)_f$—O—$]_y$—$(CH_2)_g$—OR', wherein, independently, d is 0, or an integer from 1 to 10, e is 0, or an integer from 1 to 10, f is 1 to 10, g is 1 to 10, x and y are each independently 1 or 0, and R' is either H or a hydrocarbyl group as defined previously, provided that when e is 0, then x is 0; when f is 0, then y is 0; when e is not 0, then x is 1; and when f is not 0, then y is 1. Preferably the polyalkylene oxide is polyethylene oxide. Polyethylene oxide is defined according to the formula —$(CH_2)_d$—O—$[(CH_2)_e$—O—$]_x$—$[(CH_2)_f$—O—$]_y$—$(CH_2)_g$—OR', wherein, independently, d is 0 or 2, e is 0 or 2, f is 0 or 2, g is 2, x and y are each independently 1 or 0, and R' is either H or an ethyl group, provided that when e is 0, then x is 0; when f is 0, then y is 0; when e is not 0, then x is 1; and when f is not 0, then y is 1.

In preferred embodiments of the invention, Y is in the meta position.

M can be a monovalent ion and may be selected from $Li^{+1}$, $Na^{+1}$, $K^{+1}$, $Cu^{+1}$, $Ag^{+1}$, $Au^{+1}$, and $Tl^{+1}$. Preferably M is copper. When M is a single monovalent metal ion, the resulting porphyrin-metal complex anion is charge-balanced by a counter cation. Preferably the counter cation is selected from any of the foregoing monovalent metal ions, and ammonium and phosphonium cations. Preferably the counter cation is selected from tetramethylammonium, tetrabutylammonium, tetraphenylammonium, tetramethylphosphonium, tetrabutylphosphonium, and tetraphenylphosphonium. The counter cation may be either bound or associated in some form with the porphyrin-metal complex.

M can be a divalent metal ion. Preferably the divalent metal ion is selected from $V^{2+}$, $Mn^{2+}$, $Fe^{2+}$, $Ru^{2+}$, $Co^{2+}$, $Ni^{2+}$, $Cu^{2+}$, $Pd^{2+}$, $Pt^{2+}$, $Zn^{2+}$, $Ca^{2+}$, $Mg^{2+}$, $Sr^{2+}$, and $Ba^{2+}$.

M can be a trivalent metal ion. Preferably the trivalent metal ion is selected from $Gd^{3+}$, $Y^{3+}$, $In^{3+}$, $Cr^{3+}$, $Ga^{3+}$, $Al^{3+}$, $Eu^{3+}$, and $Dy^{3+}$.

M can also be a tetravalent metal ion. Preferably the tetravalent metal ion is selected from $Tc^{4+}$, $Ge^{4+}$, $Sn^{4+}$, and $Pt^{4+}$.

M can be a pentavalent metal ion. Preferably the pentavalent metal ion is $Tc^{5+}$.

M may also be a hexavalent metal ion. Preferably the hexavalent metal ion is selected from $W^{6+}$, $Tc^{6+}$, and $Mo^{6+}$.

Preferably, M is a divalent or trivalent metal ion.

Preferably, the resulting porphyrin-metal complex cation is charge-balanced by an appropriate number of counter anions, which may be monoanions, dianions, or trianions. Preferably a porphyrin-metal complex cation derived from a trivalent metal ion may be charge-balanced by a single counter monoanion, and such a complex derived from a tetravalent metal ion may, preferably, be charge-balanced by a single counter dianion or two counter monoanions, and so on.

Suitable counter monoanions include chloride, perchlorate, sulfate, nitrate, and tetrafluoroborate. Preferably the counter dianion is selected from oxide, sulfide, or a porphyrin compound containing a divalent negative charge. The porphyrin compound containing a divalent negative charge may be a porphyrin compound of the present invention with the proviso that M is absent. Preferably the counter trianion is phosphate.

The counter monoanion, dianion, or trianion may be either bound or associated in some form with a carborane-containing porphyrin compound of the present invention. Preferably the carborane-containing porphyrin compound may also be bound to or associated with neutrally charged molecules, such as molecules of solvation, for example, water, acetonitrile, methanol, and so on.

M can be a radioactive metal ion imageable by single photon emission computed tomography (SPECT) or positron emission tomography (PET). Some examples of radioactive metals suitable for SPECT are $^{67}Cu$, $^{99m}Tc$, $^{111}In$, and those for PET include $^{64}Cu$, $^{55}Co$. Preferably M is a radioactive metal useful as a radiopharmaceutical for therapy. Some examples of radioactive metals suitable for such therapy include $^{90}Y$, $^{188}Re$ and $^{67}Cu$.

M is suitably a paramagnetic metal ion detectable by magnetic resonance imaging (MRI). Preferably the paramagnetic metal ion is selected from Mn, Fe, Co, and Gd.

Preferably $R_{10}$ and $R_{11}$ are hydrogen.

Preferably r is 1 to 10, more preferably 1 to 6, more preferably 1.

Preferably a is 2 or 1, more preferably 1.

Z is preferably selected from the carboranes —$C_2HB_9H_{10}$ or —$C_2HB_{10}H_{10}$, wherein —$C_2HB_9H_{10}$ is nido ortho-, meta-, or para-carborane, and —$C_2HB_{10}H_{10}$ is closo ortho-, meta-, or para-carborane. Z can comprise 2 carbon atoms and 10 boron atoms within a cage structure.

In one particular embodiment, two of $R^1$, $R^2$, $R^3$, and $R^4$ are substituents represented by formula (2); a is 1; Y is represented by —X—$(CR^{10}R^{11})_r$—Z; $R^{10}$ and $R^{11}$ are H; r is 1; Z is —$C_2HB_{10}H_{10}$; the —X—$(CR^{10}R^{11})_r$—Z substituents are in the meta positions of the phenyl rings; the two $R^1$-$R^4$ not represented by formula (2) are —$NO_2$ or —Br; and the substituents represented by formula (2) are in the cis conformation on the porphyrin ring.

In another particular embodiment, two of $R^1$, $R^2$, $R^3$, and $R^4$ are substituents represented by formula (2); a is 1; Y is represented by —X—$(CR^{10}R^{11})_r$—Z; $R^{10}$ and $R^{11}$ are H; r is 1; Z is —$C_2HB_{10}H_{10}$; the —X—$(CR^{10}R^{11})_r$—Z substituents are in the meta positions of the phenyl rings; the two $R^1$-$R^4$ not represented by formula (2) are —$NO_2$ or —Br; and the substituents represented by formula (2) are in the trans conformation on the porphyrin ring.

When the porphyrin compound requires a counter dianion, the counter dianion may be a porphyrin compound containing a divalent negative charge. The porphyrin compound containing a divalent negative charge may be a carborane-containing porphyrin compound of the present invention, with the proviso that M is absent.

In a specific embodiment, described in more detail below, the compound is copper meso-5,15-bis[3-[(1,2-dicarba-closo-dodecaboranyl)methoxy]phenyl]-meso-10,20-dinitroporphyrin(="MTL005").

The pharmaceutical compositions of the invention comprise:

(a) a compound of the formula (1), or a subset or embodiment thereof as hereinbefore defined; and (b) a vehicle comprising:

(i) N,N-dimethylacetamide as solvent; and (ii) a co-solvent comprising one or more pharmaceutically acceptable glycol or surfactant components.

The surfactant may be cationic, anionic or non-ionic. In embodiments described in more detail below, the surfactant is non-ionic.

It has been found that by formulating the compound of formula (1) in a vehicle comprising N,N-dimethylacetamide and the co-solvent, it is possible to maintain the compound of formula (1) in solution and minimise or prevent precipitation of the compound when the composition is diluted with an aqueous diluent, such as buffered saline solutions used for infusions, unbuffered saline, water for injection, vehicles comprising saline, vehicles comprising dextrose and other vehicles comprising one or more salts or sugars.

Thus, the compositions of the invention are particularly suitable for administration by infusion or injection. In use of the compositions they may be infused, preferably slowly and carefully infused, into a patient prior to irradiation. Infusion rate may be modified and adjusted according to the patient being treated, and the rate changed accordingly. Slower rates can avoid some adverse reaction, e.g. pain reactions to over-rapid infusion of a large volume of composition.

The compound N,N-dimethylacetamide may be referred to herein for convenience as dimethylacetamide or simply DMA.

The co-solvent (ii) comprises one or more pharmaceutically acceptable glycol or surfactant components. By "pharmaceutically acceptable" is meant that the glycols are acceptable for use in human medicine and are essentially non-toxic to humans in the concentrations at which they are used. Thus glycols such as ethylene glycol and diethylene glycol, which are toxic to humans, are not included in the definition of pharmaceutically acceptable glycols.

Simple pharmaceutically acceptable glycols that can be used in the compositions of the invention include propylene glycol.

The term pharmaceutically acceptable glycols also includes polyethylene glycols (optionally in the molecular weight range PEG200-600) and derivatives of polyethylene glycols such as tetraglycol (also known as glycofurol, also referred to as tetra ethylene glycol or TTEG).

Examples of polyethylene glycols are those that exist as liquids at around room temperature (e.g. 25° C.), for example polyethylene glycols having an average molecular weight of 200 to 400. Particular polyethylene glycols are those having an average molecular weight of about 300.

Examples of non-ionic surfactants include polyoxyethylene sorbitan monoesters; polyoxyethylene esters of hydroxylated fatty acids; poloxamers; and polyethoxylated glycerides such as polyethoxylated castor oil.

The polyoxyethylene sorbitan monoester can be, for example, polyoxyethylene sorbitan monolaurate (polysorbate 20) or polyoxyethylene sorbitan monooleate (polysorbate 80).

Examples of polyoxyethylene esters of a hydroxylated fatty acid include polyoxyethylene 15-hydroxystearate which is commercially available as Solutol® HS15.

The vehicle (b) may comprise 10-99%, optionally 55-90% (v/v) of solvent (i) and 1-90%, optionally 10-45% (v/v) of co-solvent (ii).

More particularly, the vehicle (b) may comprise 55-85% (v/v) of solvent (i) and 15-45% (v/v) of co-solvent (ii).

In one embodiment, the vehicle (b) comprises 58-85% (v/v) of solvent (i) and 15-42% (v/v) of co-solvent (ii).

In another embodiment, the vehicle (b) comprises 60-85% (v/v) of solvent (i) and 15-40% (v/v) of co-solvent (ii).

In a further embodiment, the vehicle (b) comprises 65-85% (v/v) of solvent (i) and 15-35% (v/v) of co-solvent (ii).

In another embodiment, the vehicle (b) comprises 65-82% (v/v) of solvent (i) and 18-35% (v/v) of co-solvent (ii).

In another embodiment, the vehicle (b) comprises 68-82% (v/v) of solvent (i) and 18-32% (v/v) of co-solvent (ii).

In another embodiment, the vehicle (b) comprises 69-81% (v/v) of solvent (i) and 19-31% (v/v) of co-solvent (ii).

In more particular embodiments, the co-solvent (ii) comprises:
- (ii-a) polyoxyethylene 15-hydroxystearate; or
- (ii-b) a mixture of polyoxyethylene 15-hydroxystearate and polyethylene glycol; or
- (ii-c) polysorbate 20; or
- (ii-d) polyethylene glycol; or
- (ii-e) a mixture of polysorbate 20 and polyethylene glycol; or
- (ii-f) a mixture of polysorbate 20 and propylene glycol; or
- (ii-g) tetraglycol; or
- (ii-h) a mixture of polysorbate 20 and tetraglycol; or
- (ii-i) a mixture of polyoxyethylene 15-hydroxystearate and tetraglycol;

wherein the amount of co-solvent, relative to the solvent, may be as defined in any of the foregoing embodiments.

In one preferred embodiment, the co-solvent (ii) comprises polyoxyethylene 15-hydroxystearate or a mixture of polyoxyethylene 15-hydroxystearate and polyethylene glycol.

For example, the vehicle (b) can comprise 68-82% (v/v) of the solvent (i) dimethylacetamide and 18-32% (v/v) of the co-solvent (ii) wherein the co-solvent (ii) comprises polyoxyethylene 15-hydroxystearate and optionally polyethylene glycol. In this embodiment, the polyethylene glycol, when present, may constitute from 1-15% (v/v) of the vehicle (b), and more particularly from 8-12% (v/v) of the vehicle (b).

In a further preferred embodiment, the vehicle (b) can comprise 68-82% (v/v) of the solvent (i) dimethylacetamide and 18-32% (v/v) of the co-solvent (ii) wherein the co-solvent (ii) consists of polyoxyethylene 15-hydroxystearate or a 2:1 (v/v) mixture of polyoxyethylene 15-hydroxystearate and polyethylene glycol.

In each of the foregoing embodiments, particular grades of polyethylene glycol are those polyethylene glycols having an average molecular weight of 200 to 400 and, more particularly, those having an average molecular weight of about 300

The compound of formula (1) is typically present in the pharmaceutical compositions of the invention in an amount corresponding to from 1 mg, optionally from 5 mg, optionally from 25 mg to 100 mg per millilitre of the vehicle (b), more typically from 40 mg to 80 mg per millilitre of the vehicle (b).

For example, in one embodiment, the compound of formula (1) is present in an amount corresponding to approximately 50 mg per millilitre of the vehicle (b).

In another embodiment, the compound of formula (1) is present in an amount corresponding to approximately 75 mg per millilitre of the vehicle (b).

The pharmaceutical compositions of the invention as hereinbefore defined may take the form of a solution of the compound of formula (1) in the vehicle (b). Such solutions can be used for administration of the compound of formula (1) by injection or they can be diluted with an aqueous medium to form a solution for administration by infusion.

In an alternative embodiment, the pharmaceutical compositions can comprise a first container containing the compound of formula (1) in a dried particulate (e.g. powder, lyophilised powder or freeze dried powder) form and one or more further containers containing the solvent (i) and co-solvent (ii). For example, there can be two further containers, one of which contains solvent (i) and the other of which contains a mixture of solvent (i) and co-solvent (ii). Into the dimethylacetamide solvent the co-solvent or a mixture of solvent and co-solvent can be added to complete the composition. Reconstitutable compositions of this type are particularly suitable where the compound of formula (1) does not have good long term stability in aqueous solution.

In each of the foregoing embodiments of the invention, the compound of formula (1) may be copper meso-5,15-bis[3-[(1,2-dicarba-closo-dodecaboranyl)methoxy]-phenyl]-meso-10,20-dinitroporphyrin.

The compositions of the invention can be used as radiosensitisers in the treatment of cancers, for example as described in WO2008/133664.

Accordingly, in another aspect, the invention provides a composition comprising a compound of the formula (1) and a vehicle comprising a solvent (i) and co-solvent (ii) as defined herein for use as a radiosensitiser.

In another aspect, the invention provides a composition comprising a compound of the formula (1) and a vehicle comprising a solvent (i) and co-solvent (ii) as defined herein for use as a radiosensitiser in the treatment of cancer.

In another aspect, the invention provides a composition comprising a compound of the formula (1) and a vehicle comprising a solvent (i) and co-solvent (ii) as defined herein for use in combination with radiotherapy in the treatment of cancer.

In another aspect, the invention provides a method of sensitising a tumour to radiation treatment, which method comprises administering to a patient in need thereof an effective radiation sensitising amount of a composition comprising a compound of the formula (1) and a vehicle comprising a solvent (i) and co-solvent (ii) as defined herein.

The use of a vehicle comprising a solvent (i) and co-solvent (ii) assists in solubilising the compound of formula (1) in aqueous media so that it can be administered by injection, infusion, perfusion or instillation, etc.

Accordingly, in a further aspect, the invention provides a solution for injection or infusion which comprises a compound of the formula (1) a vehicle comprising a solvent (i) and co-solvent (ii) as hereinbefore defined; and an aqueous diluents, e.g. an isotonic aqueous diluent.

The isotonic aqueous diluents may be buffered or unbuffered; optionally they are buffered to a physiologically acceptable pH (for example a pH in the range from 7 to 7.5). The aqueous diluents are present, in one embodiment, at a ratio of approximately 1:1 with the vehicle; more generally, the diluents may be present in a volume from about 0.3 times to at least ten times (more usually at least 100 times, and up to 200 times) that of the vehicle.

Further aspects and embodiments of the invention will be apparent from the following non-limiting examples.

EXAMPLES

Example 1

Solubility of copper meso-5,15-bis[3-[(1,2-dicarba-closo-dodecaboranyl)-methoxy]-phenyl]-meso-10,20-dinitroporphyrin in Water-Miscible Solvents Copper meso-5,15-bis[3-[(1,2-dicarba-closo-dodecaboranyl)-methoxy]-phenyl]-meso-10,20-dinitroporphyrin (referred to below for convenience as MTL-005) is typically administered by injection or infusion and therefore the solvents present in any liquid formulation of MTL-005 will need to be miscible with water.

Initial solubility screening tests were therefore carried out to determine the solubility of MTL-005 in various water-miscible solvents. The screening tests were carried out by dissolving the MTL-005 in the test solvent, filtering the resulting solution to remove any undissolved materials and assaying the filtrate by measuring the UV absorbance at 420.6 nm. The results are shown in Table 1 below.

TABLE 1

| Solvent | Total MTL-005 dissolved (mg/ml) |
|---|---|
| Deionised water | 0.001 |
| Absolute ethanol | 0.089 |
| Polysorbate 20 | 5.88* |
| Polysorbate 20 (5% w/v aq) | 0.27 |
| Polysorbate 20 (10% w/v aq) | 0.13 |
| Polysorbate 20 (20% w/v aq) | 0.13 |
| Polysorbate 80 (5% w/v aq) | 0.15 |
|  | 0.22 |
| Polysorbate 80 (10% w/v aq) | 0.25 |
| Polysorbate 80 (20% w/v aq) | 0.38 |
| Benzyl alcohol | 0.91 |
| N,N-Dimethylacetamide (DMA) | 74.08* |
| DMA 10% w/v aq | 0.13 |
| Solutol HS15 | 11.50 |
| Solutol HS15 (5% w/v aq) | 0.08 |
| Solutol HS15 (10% w/v aq) | 0.10 |
| Solutol HS15 (20% w/v aq) | 0.16 |
| Soyabean oil | 0.59 |
| pH 7 Britton Robinson buffer | 0.0016 |
| Macrogol 300 | 2.60 |
| Propylene glycol | 0.019 |
| Glycofurol | 8.68 |
| Cremophor EL 5% aq | 0.24 |
| Cremophor EL 10% aq | 0.27 |
| Cremophor EL 10% aq(heated) | 1.65 |
| DMA diluted 1 in 10 with Solutol HS15 20% w/v aq | 1.44 |
| Polysorbate 80 5%, DMA 10% aq | 0.45 |
| Polysorbate 80 5%, Cremophor EL 5% aq | 0.28 |
| DMA 10%, Cremophor EL 5% aq | 0.30 |
| Polysorbate 80 5%, DMA 10%, Cremophor EL 5% aq | 0.35 |

Notes:
*Results were close to the concentration of MTL-005 in the samples, and solubility results may therefore be greater than those stated.
Vehicles are made up to volume with water unless otherwise stated.

The initial screening tests showed that N,N-dimethylacetamide was by far the best solvent tested.

Solubility of copper meso-5,15-bis[3-[(1,2-dicarba-closo-dodecaboranyl)-methoxy]-phenyl]-meso-10,20-dinitroporphyrin in Aqueous DMA Mixtures In order to assess the suitability of DMA solutions of MTL-005 for administration by aqueous infusion, the solubility of MTL-005 in mixtures of DMA and water was assessed using the assay method described above. The results are shown in Table 2 below.

TABLE 2

| Vehicle | Quantity added (mg/ml) | Solubility (mg/ml) |
|---|---|---|
| 100% DMA | 92.5 | >90 |
| 80% DMA/20% Water | 18 | <0.05 |
| 60% DMA/40% Water | 20 | <0.05 |
| 40% DMA/60% Water | 5 | <0.05 |
| 20% DMA/80% Water | 5 | <0.05 |

The results demonstrate that although MTL-005 is highly soluble in DMA, its solubility decreases sharply in the presence of water, and therefore solutions of MTL-005 in DMA alone would be unlikely to be suitable for administration by infusion.

Solubility of copper meso-5,15-bis[3-[(1,2-dicarba-closo-dodecaboranyl)-methoxy]-phenyl]-meso-10,20-dinitroporphyrin in DMA/Cosolvent Mixtures According to the invention, water-miscible co-solvents are added to the DMA in order to improve the solubility of the MTL-005 when the formulation is diluted with water. Tests were therefore carried out to determine the solubility of MTL-005 in various DMA/co-solvent mixtures using the methods described above.

In the first series of tests, approximately 50 mg/ml MTL-005 was added to a range of cosolvent vehicles. A solubility in the region of 50 mg/ml was obtained for a range of vehicles (see results in column 1 in Table 3 below), therefore it could not be confirmed that saturated solutions were obtained. The work was therefore repeated at a higher MTL-005 loading of 150 mg/ml (see results in column 2 of Table 3).

TABLE 3

| Cosolvent System | | Total MTL-005 dissolved (mg/ml) (50 mg/ml added) | Total MTL-005 dissolved (mg/ml) (150 mg/ml added) |
|---|---|---|---|
| Two-Component Systems | | | |
| DMA 80% | Tween 20 20% | 51 | 91 |
| DMA 60% | Tween 20 40% | 47 | 37 |
| DMA 80% | Solutol HS 20% | 49 | 115 |
| DMA 70% | Solutol HS 30% | n.d | 70 |
| DMA 60% | Solutol HS 40% | 51 | 58 |
| DMA 80% | Macrogol 300 20% | 50 | 76 |
| DMA 60% | Macrogol 300 40% | 34 | n.d |

TABLE 3-continued

| Cosolvent System | | Total MTL-005 dissolved (mg/ml) (50 mg/ml added) | Total MTL-005 dissolved (mg/ml) (150 mg/ml added) |
|---|---|---|---|
| DMA 80% | Propylene Glycol 20% | 27 | n.d |
| DMA 60% | Propylene Glycol 40% | 4 | n.d |
| DMA 80% | Tetraglycol 20% | 52 | 131 |
| DMA 60% | Tetraglycol 40% | 53 | 94 |
| Three Component Systems* | | | |
| DMA 80% | Tween 20 10% Solutol HS 10% | 52 | n.d |
| DMA 80% | Tween 20 10% Macrogol 300 10% | 50 | 83 |
| DMA 80% | Tween 20 10% Propylene Glycol 10% | 49 | 79 |
| DMA 80% | Tween 20 10% Tetraglycol 10% | 48 | 101 |
| DMA 80% | Solutol HS 10% Macrogol 300 10% | 49 | 95 |
| DMA 70% | Solutol HS 20% Macrogol 300 10% | n.d | 74 |
| DMA 80% | Solutol HS 10% Propylene Glycol 10% | 50 | 58 |
| DMA 80% | Solutol HS 10% Tetraglycol 10% | 49 | 113 |
| DMA 80% | Macrogol 300 10% Propylene Glycol 10% | 48 | n.d |
| DMA 80% | Macrogol 300 10% Tetraglycol 10% | 49 | n.d |
| DMA 80% | Tetraglycol 10% Propylene Glycol 10% | 50 | n.d |

Notes:
*The amount of MTL-005 added to each sample was approx 50 mg/ml. Therefore results in the region of this value may not be saturated solubilities.
n.d—not determined
Note:
Tetraglycol is also known as Glycofural.

Formulations Containing copper meso-5,15-bis[3-[(1,2-dicarba-closo-dodeca-boranyl)-methoxy]-phenyl]-meso-10,20-dinitroporphyrin in DMA/Cosolvent Mixtures Based on the results set out in Table 3, various formulations containing MTL-005 and a DMA/co-solvent mixture were prepared. The details of the formulations are shown in Table 4.

TABLE 4

| Formulation | Concentration of MTL-005 | Solvent (% v/v of total vehicle volume) | Co-Solvent (% v/v of total vehicle volume) |
|---|---|---|---|
| 1 | 50 mg/ml | DMA (80%) | Polysorbate 20 (20%) |
| 2 | 50 mg/ml | DMA (80%) | Solutol HS15 (20%) |
| 3 | 50 mg/ml | DMA (80%) | Macrogol 300 (20%) |
| 4 | 50 mg/ml | DMA (80%) | Tetraglycol (20%) |
| 5 | 50 mg/ml | DMA (60%) | Tetraglycol (40%) |
| 6 | 50 mg/ml | DMA (80%) | Polysorbate 20 (10%) & Macrogol 300 (10%) |
| 7 | 50 mg/ml | DMA (80%) | Polysorbate 20 (10%) & Propylene glycol (10%) |
| 8 | 50 mg/ml | DMA (80%) | Polysorbate 20 (10%) & Tetraglycol (10%) |
| 9 | 50 mg/ml | DMA (80%) | Solutol HS15 (10%) & Macrogol 300 (10%) |
| 10 | 50 mg/ml | DMA (80%) | Solutol HS15 (10%) & Tetraglycol (10%) |
| 11 | 75 mg/ml | DMA (90%) | Solutol HS15 (10%) |
| 12 | 75 mg/ml | DMA (80%) | Solutol HS15 (20%) |
| 13 | 75 mg/ml | DMA (70%) | Solutol HS15 (30%) |
| 14 | 75 mg/ml | DMA (70%) | Solutol HS15 (20%) & Macrogol 300 (10%) |
| 15 | 50 mg/ml | DMA (70%) | Solutol HS15 (30%) |
| 16 | 50 mg/ml | DMA (70%) | Solutol HS15 (20%) & Macrogol 300 (10%) |

Static Dilution Study I—Formulations 1 to 10 of Table 4

In order to mimic their behaviour on slow intravenous administration, formulations were tested using a static dilution method (see Ping et al., *J. Pharm. Sci.*, 1998; February: 87(2): 196-199). The tests were conducted by preparing formulations containing 50 mg/ml of the MTL-005 and adding 1 ml volumes of a formulation to 10 ml, 100 ml and 1000 ml volumetric flasks that had been prefilled with Sorensen's isotonic phosphate buffer (ISPB, pH 7.4). The samples were shaken and filtered and diluted as necessary in DMA in order to achieve a suitable UV absorbance reading. From the UV readings, the concentrations of MTL-005 remaining in solution after dilution and filtration were calculated and the results are shown in Table 5 below.

TABLE 5

| Formulation | Dilution | MTL-005 conc. (mg/ml) | MTL-005 conc. as % of nominal * |
|---|---|---|---|
| Formulation 1 | Diluted 1 ml + 10 ml pH 7.4 buffer | 0.440 | 9.7 |
| " | Diluted 1 ml + 100 ml pH 7.4 buffer | 0.122 | 24.4 |
| " | Diluted 1 ml + 1000 ml pH 7.4 buffer | 0.035 | 70.0 |
| Formulation 2 | Diluted 1 ml + 10 ml pH 7.4 buffer | 4.036 | 88.7 |
| " | Diluted 1 ml + 100 ml pH 7.4 buffer | 0.510 | 102 |
| " | Diluted 1 ml + 1000 ml pH 7.4 buffer | 0.067 | 134 |
| Formulation 3 | Diluted 1 ml + 10 ml pH 7.4 buffer | 0.015 | 0.3 |
| " | Diluted 1 ml + 100 ml pH 7.4 buffer | 0.017 | 3.4 |
| " | Diluted 1 ml + 1000 ml pH 7.4 buffer | 0.022 | 44 |

TABLE 5-continued

| Formulation | Dilution | MTL-005 conc. (mg/ml) | MTL-005 conc. as % of nominal * |
|---|---|---|---|
| Formulation 4 | Diluted 1 ml + 10 ml pH 7.4 buffer | 0.021 | 0.5 |
| " | Diluted 1 ml + 100 ml pH 7.4 buffer | 0.026 | 5.2 |
| " | Diluted 1 ml + 1000 ml pH 7.4 buffer | 0.021 | 42 |
| Formulation 5 | Diluted 1 ml + 10 ml pH 7.4 buffer | 0.020 | 0.4 |
| " | Diluted 1 ml + 100 ml pH 7.4 buffer | 0.021 | 4.2 |
| " | Diluted 1 ml + 1000 ml pH 7.4 buffer | 0.021 | 42 |
| Formulation 6 | Diluted 1 ml + 10 ml pH 7.4 buffer | 0.172 | 3.8 |
| " | Diluted 1 ml + 100 ml pH 7.4 buffer | 0.117 | 23.4 |
| " | Diluted 1 ml + 1000 ml pH 7.4 buffer | 0.039 | 78 |
| Formulation 7 | Diluted 1 ml + 10 ml pH 7.4 buffer | 0.160 | 3.5 |
| " | Diluted 1 ml + 100 ml pH 7.4 buffer | 0.132 | 26.4 |
| " | Diluted 1 ml + 1000 ml pH 7.4 buffer | 0.055 | 110 |
| Formulation 8 | Diluted 1 ml + 10 ml pH 7.4 buffer | 0.258 | 5.7 |
| " | Diluted 1 ml + 100 ml pH 7.4 buffer | 0.138 | 27.6 |
| " | Diluted 1 ml + 1000 ml pH 7.4 buffer | 0.029 | 58 |
| Formulation 9 | Diluted 1 ml + 10 ml pH 7.4 buffer | 0.617 | 13.6 |
| " | Diluted 1 ml + 100 ml pH 7.4 buffer | 0.221 | 44.2 |
| " | Diluted 1 ml + 1000 ml pH 7.4 buffer | 0.048 | 96 |
| Formulation 10 | Diluted 1 ml + 10 ml pH 7.4 buffer | 0.634 | 13.9 |
| " | Diluted 1 ml + 100 ml pH 7.4 buffer | 0.369 | 73.8 |
| " | Diluted 1 ml + 1000 ml pH 7.4 buffer | 0.059 | 118 |

* In the 1 in 11 dilution, the nominal MTL-005 concentration is 4.55 mg/ml.
In the 1 in 101 dilution, the nominal MTL-005 concentration is 0.50 mg/ml.
In the 1 in 1001 dilution, the nominal MTL-005 concentration is 0.05 mg/ml.

The results demonstrate that adding one or two water-miscible co-solvent to the DMA improves the solubility of the MTL-005 when the formulation is diluted with aqueous solutions.

Static Dilution Study II—Formulations 2 and 11 to 16 of Table 4

Formulations 2 and 11 to 16 of Table 4 were subjected to a static dilution test following the general method described for static dilution test I but using dilutions with 10 ml, 100 ml and 250 ml of Sorensen's pH 7.4 isotonic phosphate buffer. The results are shown in Table 6 below.

TABLE 6

| Formulation | Dilution | MTL-005 conc. (mg/ml) | MTL-005 conc. as % of nominal * |
|---|---|---|---|
| Formulation 11 | Diluted 1 ml + 10 ml pH 7.4 buffer | 0.338 | 5 |
| " | Diluted 1 ml + 100 ml pH 7.4 buffer | 0.072 | 10 |
| " | Diluted 1 ml + 250 ml pH 7.4 buffer | 0.038 | 13 |
| Formulation 12 | Diluted 1 ml + 10 ml pH 7.4 buffer | 2.813 | 41 |
| " | Diluted 1 ml + 100 ml pH 7.4 buffer | 0.568 | 77 |
| " | Diluted 1 ml + 250 ml pH 7.4 buffer | 0.266 | 89 |
| Formulation 13 | Diluted 1 ml + 10 ml pH 7.4 buffer | 6.044 | 89 |
| " | Diluted 1 ml + 100 ml pH 7.4 buffer | 0.727 | 98 |
| " | Diluted 1 ml + 250 ml pH 7.4 buffer | 0.302 | 101 |
| Formulation 14 | Diluted 1 ml + 10 ml pH 7.4 buffer | 1.429 | 21 |
| " | Diluted 1 ml + 100 ml pH 7.4 buffer | 0.673 | 91 |
| " | Diluted 1 ml + 250 ml pH 7.4 buffer | 0.286 | 95 |
| Formulation 2 | Diluted 1 ml + 10 ml pH 7.4 buffer | 4.004 | 88 |
| " | Diluted 1 ml + 100 ml pH 7.4 buffer | 0.539 | 108 |
| " | Diluted 1 ml + 250 ml pH 7.4 buffer | 0.232 | 116 |
| Formulation 15 | Diluted 1 ml + 10 ml pH 7.4 buffer | 4.648 | 102 |
| " | Diluted 1 ml + 100 ml pH 7.4 buffer | 0.488 | 98 |
| " | Diluted 1 ml + 250 ml pH 7.4 buffer | 0.265 | 133 |
| Formulation 16 | Diluted 1 ml + 10 ml pH 7.4 buffer | 2.795 | 61 |
| " | Diluted 1 ml + 100 ml pH 7.4 buffer | 0.515 | 103 |
| " | Diluted 1 ml + 250 ml pH 7.4 buffer | 0.219 | 110 |

* In the 1 in 11 dilution of Formulations 11 to 14, the nominal MTL-005 concentration is 6.82 mg/ml.
In the 1 in 101 dilution of Formulations 11 to 14, the nominal MTL-005 concentration is 0.74 mg/ml.
In the 1 in 251 dilution of Formulations 11 to 14, the nominal MTL-005 concentration is 0.30 mg/ml.
In the 1 in 11 dilution of Formulations 2, 15 and 16, the nominal MTL-005 concentration 4.55 mg/ml).
In the 1 in 101 dilution of Formulations 2, 15 and 16, the nominal MTL-005 concentration is 0.50 mg/ml.
In the 1 in 251 dilution of Formulations 2, 15 and 16, the nominal MTL-005 concentration 0.20 mg/ml.

The results shown in Table 6 show that in formulations containing DMA and at least 20% (v/v) of a co-solvent, the solubility of MTL-005 is greatly increased when a water-miscible co-solvent is included in an amount of at least 20% by volume of the total volume of the vehicle. Improved solubility is also demonstrated when only 10% of a co-solvent is present (see formulation 11) but to a significantly lower extent.

Formulations where there is no significant loss of solubility of the MTL-005 when the formulation is diluted with an aqueous medium such as isotonic phosphate buffered saline medium can be used for administration of MTL-005 by infusion.

Example 2

Formulation for Reconstitution

Stability studies have shown that copper meso-5,15-bis[3-[(1,2-dicarba-closo-dodecaboranyl)-methoxy]-phenyl]-meso-10,20-dinitroporphyrin (MTL-005) is not stable for extended periods in solution, although it is relatively stable as a dry powder.

Therefore, the formulations can be presented in the form of a kit comprising the MTL-005 in dried particulate (e.g. powder) form together with one or more containers containing the solvent and/or co-solvent or co-solvents.

A kit from which Formulation 16 can be prepared comprises the following components:

(i) a stoppered 30 ml clear glass vial containing 515 mg of copper meso-5,15-bis[3-[(1,2-dicarba-closo-dodecaboranyl)-methoxy]-phenyl]-meso-10,20-dinitroporphyrin (MTL-005);

(ii) a 10 ml clear glass ampoule containing 5.50 ml of N,N-dimethylacetamide (DMA); and (iii) a 20 ml clear glass ampoule containing 4.27 g of Solutol HS15 (equivalent to 27.0% w/v), 2.05 g of Macrogol 300 (equivalent to 13.0 w/v) and sufficient dimethylacetamide to give a total volume of 15.8 ml.

In use, the contents of (i) and (ii) are combined so the DMA dissolves the MTL-005. Once the MTL-005 has completely dissolved, ampoule (iii) is broken open and the contents mixed with the MTL-005/DMA solution to give the final solution for administration directly by injection or for dilution in saline for administration by infusion.

Example 3

Protocol for Administration in Cancer Therapy

Initial infusion studies in rat and dog models were carried out, confirming no adverse pain or toxicology events during infusion of formulation 16 referred to above and the following protocol for human administration developed:

Protocol

The formulation is prepared as soon as possible prior to commencement of infusion, and generally no longer than three hours beforehand.

The rate of infusion is 0.25 mL/kg/hour of formulation, 16 containing 12.5 mg MTL-005 per mL.

The infusion rate may be reduced at the discretion of the physician, but the total duration of infusion should not exceed four hours.

The site of peripheral intravenous cannulation is also at the discretion of the physician.

Doses of 2, 4, 6.6, 10, 14 and 18 mg/kg may be given.

Doses of 2, 4 and 6.6 mg/kg correspond to infusion durations of approximately 38, 77 and 127 minutes.

Doses of 10, 14 and 18 mg/kg correspond to two equal infusion periods each of approximately 96, 134 and 173 minutes.

The infusion is followed by a cycle of radiotherapy or chemoradiotherapy.

Equivalents

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A pharmaceutical composition comprising:
(a) a compound of the formula (1):

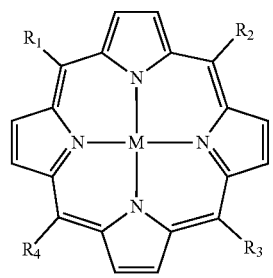

(1)

wherein:
$R^1$, $R^2$, $R^3$, and $R^4$ are selected from an electron withdrawing group, —$NO_2$, —$NH_2$, halogen, and a substituent represented by the following formula

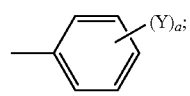

(2)

wherein Y can be on the ortho, meta or para position on the phenyl rings, and is selected from hydrogen, hydrocarbyl, non-aromatic carbocyclic, non-aromatic heterocyclic, aryl, alkylaryl, arylalkyl; or a hydrocarbyl, non-aromatic carbocyclic, non-aromatic heterocyclic, aryl, alkylaryl, or a arylalkyl group substituted with 1 to 4 hydrophilic groups selected from hydroxy, alkoxy, —$C(O)OR^5$, —$SOR^6$, —$SO_2R^6$, nitro, amido, ureido, carbamato, —$SR^7$, —$NR^8R^9$, or polyalkyleneoxide; or a substituent represented by formula (3)

—X—$(CR^{10}R^{11})_r$—Z (3);

provided that at least one of $R^1$, $R^2$, $R^3$, and $R^4$ is the substituent represented by formula (2) wherein Y represents formula (3);

wherein:
X is selected from oxygen and sulfur;
$R^5$, $R^6$, $R^7$, $R^8$, $R^9$, $R^{10}$, and $R^{11}$ are selected from hydrogen and $C_1$ to $C_4$ hydrocarbyl;

Z is a carborane cluster comprising at least two carbon atoms and at least three boron atoms, or at least one carbon atom and at least five boron atoms, within a cage structure;

r is 0 or an integer from 1 to 20;

a represents an integer from 1 to 4; and provided also that at least one of $R^1$, $R^2$, $R^3$, and $R^4$ is an electron withdrawing group, $-NO_2$, $-NH_2$, or halogen; and M is selected from two hydrogen ions, a single monovalent metal ion, two monovalent metal ions, a divalent metal ion, a trivalent metal ion, a tetravalent metal ion, a pentavalent metal ion, and a hexavalent metal ion, wherein the porphyrin-metal complex derived from a single monovalent metal ion is charge-balanced by a counter cation, and the porphyrin-metal complex derived from a trivalent, tetravalent, pentavalent, or hexavalent metal ion is charge-balanced by an appropriate number of counter anions, dianions, or trianions;

(b) a vehicle comprising:
  (i) dimethylacetamide as solvent; and
  (ii) a co-solvent comprising one or more pharmaceutically acceptable glycol or non-ionic surfactant components.

2. A pharmaceutical composition according to claim 1 wherein the compound of formula (1) is copper meso-5,15-bis[3-[(1,2-dicarba-closo-dodecaboranyl) -methoxy]-phenyl]-meso-10,20-dinitroporphyrin.

3. A pharmaceutical composition according to claim 1 wherein the vehicle (b) comprises 55-90% (v/v) of solvent (i) and 10-45% (v/v) of co-solvent (ii).

4. A pharmaceutical composition according to claim 3 wherein the vehicle (b) comprises 55-85% (v/v) of solvent (i) and 15-45% (v/v) of co-solvent (ii).

5. A pharmaceutical composition according to claim 4 wherein the vehicle (b) comprises 68-82% (v/v) of solvent (i) and 18-42% (v/v) of co-solvent (ii).

6. A pharmaceutical composition according to claim 1, wherein the non-ionic surfactant is selected from a polyoxyethylene sorbitan monoester; a polyoxyethylene ester of a hydroxylated fatty acid; a poloxamers; and a polyethoxylated castor oil.

7. A pharmaceutical composition according to claim 6 wherein the polyoxyethylene sorbitan monoester is polyoxyethylene sorbitan monolaurate or polyoxyethylene sorbitan monooleate.

8. A pharmaceutical composition according to claim 6 wherein the polyoxyethylene ester of a hydroxylated fatty acid is polyoxyethylene 15-hydroxystearate.

9. A pharmaceutical composition according to claim 1, wherein the co-solvent (ii) comprises:
  (ii-a) polyoxyethylene 15-hydroxystearate; or
  (ii-b) a mixture of polyoxyethylene 15-hydroxystearate and polyethylene glycol; or
  (ii-c) polysorbate 20; or
  (ii-d) polyethylene glycol; or
  (ii-e) a mixture of polysorbate 20 and polyethylene glycol; or
  (ii-f) a mixture of polysorbate 20 and propylene glycol; or
  (ii-g) tetraglycol; or
  (ii-h) a mixture of polysorbate 20 and tetraglycol; or
  (ii-i) a mixture of polyoxyethylene 15-hydroxystearate and tetraglycol.

10. A pharmaceutical composition according to claim 9 wherein the co-solvent (ii) comprises polyoxyethylene 15-hydroxystearate or a mixture of polyoxyethylene 15-hydroxystearate and polyethylene glycol.

11. A pharmaceutical composition according to claim 10 wherein the vehicle (b) comprises 68-82% (v/v) of the solvent (i) dimethylacetamide and 18-32% (v/v) of the co-solvent (ii) wherein the co-solvent (ii) comprises polyoxyethylene 15-hydroxystearate and optionally polyethylene glycol.

12. A pharmaceutical composition according to claim 11 wherein the polyethylene glycol, when present, constitutes from 1-15% (v/v) of the vehicle (b).

13. A pharmaceutical composition according to claim 12 wherein the vehicle (b) comprises 68-72% (v/v) of the solvent (i) dimethylacetamide and 28-32% (v/v) of the co-solvent (ii) wherein the co-solvent (ii) consists of polyoxyethylene 15-hydroxystearate or a 2:1 (v/v) mixture of polyoxyethylene 15-hydroxystearate and polyethylene glycol.

14. A pharmaceutical composition according to claim 1, wherein the compound of formula (1) is present in an amount corresponding to from 25 mg to 100 mg per milliliter of the vehicle (b).

15. A pharmaceutical composition according to claim 14 wherein the compound of formula (1) is present in an amount corresponding to from 40 mg to 80 mg per milliliter of the vehicle (b).

16. A pharmaceutical composition according to claim 1, which is a solution of the compound of formula (1) in the vehicle (b).

17. A pharmaceutical composition according to claim 1 which comprises a first container containing the compound of formula (1) in a powder form and one or more further containers containing the solvent (i) and co-solvent (ii).

18. A pharmaceutical composition according to claim 17 wherein there are two further containers, one of which contains solvent (i) and the other of which contains a mixture of solvent (i) and co-solvent (ii).

19. A method of sensitising a tumour to radiation treatment, which method comprises administering to a patient in need thereof an effective radiation sensitising amount of a composition as defined in claim 1.

20. A solution for injection or infusion which comprises a compound of the formula (1), a vehicle comprising a solvent (i) and co-solvent (ii) as defined in claim 1, and an isotonic aqueous diluent.

* * * * *